US011971335B2

(12) United States Patent
Qin et al.

(10) Patent No.: US 11,971,335 B2
(45) Date of Patent: Apr. 30, 2024

(54) DEVICE FOR COLLECTING LIQUID AND SMART TOILET COMPRISING THE SAME

(71) Applicant: Shanghai Kohler Electronics, Ltd., Shanghai (CN)

(72) Inventors: Zhiyu Qin, Beijing (CN); Qintao Sun, Beijing (CN)

(73) Assignee: Shanghai Kohler Electronics, Ltd., Shanghai (CN)

(*) Notice: Subject to any disclaimer, the term of this patent is extended or adjusted under 35 U.S.C. 154(b) by 0 days.

(21) Appl. No.: 18/198,968

(22) Filed: May 18, 2023

(65) Prior Publication Data

US 2023/0288296 A1 Sep. 14, 2023

Related U.S. Application Data

(63) Continuation of application No. 17/744,198, filed on May 13, 2022, now Pat. No. 11,686,654, which is a
(Continued)

(30) Foreign Application Priority Data

Apr. 28, 2016 (CN) .......................... 201610279185.3

(51) Int. Cl.
*G01N 1/14* (2006.01)
*E03D 9/00* (2006.01)
(Continued)

(52) U.S. Cl.
CPC ................. *G01N 1/14* (2013.01); *E03D 9/00* (2013.01); *G01F 23/263* (2013.01); *G01N 33/493* (2013.01)

(58) Field of Classification Search
CPC .... G01N 1/02; G01N 1/10; G01N 2001/1031; G01N 2001/1043; G01N 1/14;
(Continued)

(56) References Cited

U.S. PATENT DOCUMENTS 2,451,704 A * 10/1948 Wood ...................... G01F 23/04
73/864.64
2,958,222 A 11/1960 Morgan
(Continued)

FOREIGN PATENT DOCUMENTS

CN 2745070 Y 12/2005
CN 201222065 Y 4/2009
(Continued)

OTHER PUBLICATIONS

ESPACENET Machine Translation of JP 2000258411, Sep. 22, 2000.
(Continued)

*Primary Examiner* — David A. Rogers
(74) *Attorney, Agent, or Firm* — Lempia Summerfield Katz LLC

(57) ABSTRACT

The present disclosure provides a method for collecting liquid comprising: collecting the liquid, by a pump body mechanism, into a cavity of a suction tube assembly; monitoring, by a liquid-level sensing mechanism, an amount of the liquid collected in the cavity; controlling, by the liquid-level sensing mechanism, a start and a stop of collecting the liquid in response to the amount of the liquid collected in the cavity; and cleaning the cavity by delivering, by the pump body mechanism, water into the cavity in response to the stop of collecting the liquid.

20 Claims, 3 Drawing Sheets

Related U.S. Application Data continuation of application No. 16/097,172, filed as application No. PCT/CN2016/103219 on Oct. 25, 2016, now Pat. No. 11,333,584.

(51) Int. Cl.
*G01F 23/263* (2022.01)
*G01N 33/493* (2006.01)

(58) Field of Classification Search
CPC ............ G01N 1/22; G01N 2001/2223; G01N 2001/2229; G01N 1/2247; G01N 1/2273
See application file for complete search history.

(56) References Cited

U.S. PATENT DOCUMENTS

| | | | |
|---|---|---|---|
| 3,315,530 A | 4/1967 | Woodley, Jr. | |
| 3,466,145 A | 9/1969 | Duyne | |
| 3,538,748 A | 11/1970 | Linsell et al. | |
| 3,581,565 A | 6/1971 | Dieterich | |
| 3,625,064 A | 12/1971 | Hinman, Jr. et al. | |
| 3,625,065 A | 12/1971 | Thompson | |
| 3,625,654 A | 12/1971 | Duyne | |
| 3,645,142 A | 2/1972 | Turpin | |
| 3,659,461 A | 5/1972 | Thompson | |
| 3,707,869 A | 1/1973 | Raynor | |
| 3,735,641 A | 5/1973 | Bink et al. | |
| 3,765,226 A | 10/1973 | Strickland et al. | |
| 3,802,270 A | 4/1974 | Daniels et al. | |
| 3,803,921 A | 4/1974 | Dieterich | |
| 3,832,904 A | 9/1974 | Lippeck et al. | |
| 3,901,087 A | 8/1975 | Fabritius | |
| 3,929,413 A | 12/1975 | Young et al. | |
| 3,940,993 A * | 3/1976 | Lapidot | G01N 1/14 73/863.02 |
| 4,018,089 A | 4/1977 | Dzula et al. | |
| 4,151,749 A * | 5/1979 | Kushner | G01N 35/00 73/864.34 |
| 4,163,392 A | 8/1979 | Deeds et al. | |
| 4,165,645 A | 8/1979 | Cooper | |
| 4,203,169 A | 5/1980 | Dale | |
| 4,252,132 A | 2/1981 | Kuntz | |
| 4,276,889 A | 7/1981 | Kuntz et al. | |
| 4,331,162 A | 5/1982 | Kuntz et al. | |
| 4,338,842 A | 7/1982 | Collins | |
| 4,418,581 A | 12/1983 | Jones | |
| 4,442,720 A | 4/1984 | Apley et al. | |
| 4,631,968 A | 12/1986 | Aske | |
| 4,636,474 A | 1/1987 | Ogura et al. | |
| 4,660,422 A | 4/1987 | Eads et al. | |
| 4,696,194 A | 9/1987 | Taylor | |
| 4,705,667 A * | 11/1987 | Marsoner | G01N 35/00594 73/864.81 |
| 4,743,155 A | 5/1988 | Carey et al. | |
| 4,771,642 A | 9/1988 | Parth et al. | |
| 4,930,360 A * | 6/1990 | Tan | C23F 1/36 73/864.34 |
| 4,961,431 A * | 10/1990 | Ikenaga | A61B 5/20 600/584 |
| 4,962,550 A | 10/1990 | Ikenaga et al. | |
| 5,029,485 A | 7/1991 | Marr | |
| 5,062,304 A | 11/1991 | Van et al. | |
| 5,111,539 A | 5/1992 | Hiruta et al. | |
| 5,118,628 A * | 6/1992 | Krumpen | G01N 33/18 436/39 |
| 5,121,641 A | 6/1992 | Silver | |
| 5,197,340 A | 3/1993 | Jones | |
| 5,218,971 A * | 6/1993 | Minami | G01F 23/20 4/304 |
| 5,224,389 A | 7/1993 | Jensen et al. | |
| 5,396,812 A | 3/1995 | Peterson | |
| 5,417,121 A * | 5/1995 | Andersen | G01N 35/1002 73/864.22 |
| 5,563,384 A | 10/1996 | Marlow et al. | |
| 5,594,222 A * | 1/1997 | Caldwell | H03K 17/962 200/600 |
| 5,625,911 A | 5/1997 | Nakayama et al. | |
| 5,720,054 A | 2/1998 | Nakayama et al. | |
| 5,730,149 A | 3/1998 | Nakayama et al. | |
| 5,844,148 A | 12/1998 | Klein et al. | |
| 6,178,830 B1 | 1/2001 | Freud | |
| 6,270,726 B1 | 8/2001 | Tyberg et al. | |
| 6,453,759 B1 | 9/2002 | Lebski et al. | |
| 6,772,450 B1 | 8/2004 | Saylor et al. | |
| 6,843,103 B2 | 1/2005 | Aguilera et al. | |
| 6,925,895 B2 * | 8/2005 | Barker | G01N 1/14 73/864.34 |
| 6,951,545 B2 | 10/2005 | Smith et al. | |
| 7,100,424 B2 | 9/2006 | Wilson | |
| 7,389,792 B2 * | 6/2008 | Newberg | F16K 41/103 137/551 |
| 7,398,702 B2 | 7/2008 | Wedell | |
| 7,430,930 B2 | 10/2008 | Zeller et al. | |
| 7,730,796 B2 | 6/2010 | Shimada et al. | |
| 7,858,041 B2 | 12/2010 | Muraishi et al. | |
| 8,096,199 B2 | 1/2012 | Riazanskaia et al. | |
| 8,312,780 B2 | 11/2012 | Blacklin et al. | |
| RE44,521 E * | 10/2013 | Musho | C12Q 1/001 205/792 |
| 8,800,393 B2 | 8/2014 | Atkinson et al. | |
| 8,935,965 B1 | 1/2015 | Selbig et al. | |
| 9,176,026 B2 | 11/2015 | Sidorsky et al. | |
| 9,851,284 B2 | 12/2017 | Atchison | |
| 10,006,838 B2 * | 6/2018 | Tokarski | G01N 1/10 |
| 10,383,606 B1 | 8/2019 | Mccord et al. | |
| 10,393,630 B2 | 8/2019 | Lemburg et al. | |
| 11,287,415 B2 * | 3/2022 | Barakat | G01N 27/27 |
| 11,402,248 B2 | 8/2022 | Gledhill et al. | |
| 2005/0124059 A1 | 6/2005 | Kureshy et al. | |
| 2008/0250857 A1 * | 10/2008 | Burdi | G01F 23/268 73/304 C |
| 2010/0058777 A1 | 3/2010 | Walter | |
| 2011/0113899 A1 | 5/2011 | Dahler et al. | |
| 2015/0218942 A1 * | 8/2015 | Lim | E21B 49/08 73/864 |
| 2015/0359522 A1 | 12/2015 | Recht et al. | |
| 2016/0116383 A1 | 4/2016 | Bernhard et al. | |
| 2016/0287155 A1 | 10/2016 | Kelly et al. | |
| 2017/0114531 A1 | 4/2017 | Ye | |
| 2018/0372717 A1 | 12/2018 | Tu et al. | |
| 2019/0170728 A1 | 6/2019 | Qin | |
| 2020/0271578 A1 | 8/2020 | Yamasaki | |
| 2020/0309646 A1 | 10/2020 | Qin et al. | |

FOREIGN PATENT DOCUMENTS

| | | |
|---|---|---|
| CN | 101551306 B | 1/2011 |
| CN | 201731946 U | 2/2011 |
| CN | 102802526 A | 11/2012 |
| CN | 204685875 U | 10/2015 |
| CN | 205157255 U | 4/2016 |
| CN | 105842013 A | 8/2016 |
| CN | 205607700 U | 9/2016 |
| CN | 206132738 U | 4/2017 |
| CN | 108713990 A | 10/2018 |
| CN | 112649239 A | 4/2021 |
| CN | 111719653 B | 5/2021 |
| DE | 20314472 U1 | 11/2003 |
| GB | 2123951 A | 2/1984 |
| JP | S51101982 U | 8/1976 |
| JP | H0584863 U | 11/1993 |
| JP | H07234217 A | 9/1995 |
| JP | 2000258411 A | 9/2000 |
| JP | 2004092385 A | 3/2004 |
| JP | 2008537775 A | 9/2008 |
| JP | 2010066263 A | 3/2010 |
| JP | 6478128 B2 | 2/2019 |
| KR | 101080828 B1 | 11/2011 |
| TW | 515719 B | 1/2003 |
| WO | 2006101833 A2 | 9/2006 |

(56) References Cited

FOREIGN PATENT DOCUMENTS

| WO | 2017185690 A1 | 11/2017 |
|---|---|---|
| WO | 2020078018 A1 | 4/2020 |
| WO | 2020099977 A1 | 5/2020 |

OTHER PUBLICATIONS

Foreign Action other than Search Report for JP Appl. Ser. No. 2019-506770 dated Jun. 26, 2020 (3 pages) (English Translation).
Foreign Action other than Search Report on JP 2019-506770 dated Oct. 8, 2019.
International Preliminary Report on Patentability for PCT Appl. Ser. No. PCT/CN2016/103219 dated Nov. 8, 2018 (14 Pages) (English Translation).
International Search Report re Application No. PCT/CN2016/103219; 6 pgs.
Japanese Office Action for JP Appl. No. 2018-239443 dated Nov. 26, 2019 (4 pages).
Japanese Office Action on JP Appl. Ser. No. 2020069588 dated March 16, 2021 (3 pages).
Korean Intellectual Property Office Notice of Preliminary Rejection dated Jul. 14, 2020 9 pages.
Korean Office Action on KR Appl. Ser. No. 10-2019-0002173 dated Oct. 15, 2020 (6 pages).

* cited by examiner

DEVICE FOR COLLECTING LIQUID AND SMART TOILET COMPRISING THE SAME

CROSS REFERENCE TO OTHER APPLICATIONS

This application is a continuation under 35 U.S.C. § 120 and 37 C.F.R. § 1.53(b) of U.S. patent application Ser. No. 17/744,198, filed May 13, 2022, which is a continuation of U.S. patent application Ser. No. 16/097,172, filed Oct. 26, 2018, which is a national stage entry of PCT/CN2016/103219, filed Oct. 25, 2016, which claims the benefit and priority of Chinese Patent Application No. 201610279185.3, filed Apr. 28, 2016, and each of which is hereby incorporated by reference in its entirety.

TECHNICAL FIELD

The present invention relates to the field of smart toilet technologies, and more particularly, to a device for collecting liquid and a smart toilet comprising the same.

BACKGROUND

Currently most urine detections are performed in hospitals after the examinees manually collect urine themselves. To perform the urine detection in hospitals, not only registrations in hospitals for treatments are required, but also hygiene problems are concerned. Moreover, some existing smart toilets perform urine detection by collecting urine from the inside surface of the toilet, causing the cross-contamination problem of the urine sample, thus the detection result is inaccurate.

Thus it can be seen that there are still obvious inconvenience and defects in the existing urine collection methods described above, further improvement is desired. How to create a new device for collecting liquid and a smart toilet comprising the same is really one of the important research and development topics at present.

SUMMARY

The technical problem to be solved in the present invention is to provide a highly automated device for collecting liquid, so that the object of collecting liquid in the air can be achieved, thereby overcoming the deficiencies of the existing urine suction devices.

In order to solve the technical problem above, the present invention provides a device for collecting liquid, which comprises a fixing support, a swinging mechanism disposed in the fixing support, a suction tube assembly connected to the swinging mechanism, and a pump body mechanism connected to the suction tube assembly.

The suction tube assembly comprises a slide rail component and a retractable suction tube component disposed in the slide rail component, one end of the slide rail component is connected to the swinging mechanism; the suction tube component comprises a suction tube, internal of which is provided with a cavity and an opening of which is disposed above the cavity; and a first conduit disposed in the suction tube, one end of the first conduit is inserted in the cavity, the other end of the first conduit is connected to the pump body mechanism; the pump body mechanism is used for pumping the liquid collected in the cavity.

As an improvement of the present invention, the device for collecting liquid further comprises a liquid-level sensing mechanism for monitoring the amount of conductive liquid collected in the cavity in real time and controlling the star and the stop of the pump body mechanism according to the amount of the liquid in the cavity.

As a further improvement, the liquid-level sensing mechanism comprises a first touch chip, a solid steel needle disposed in the suction tube with one end inserted in the cavity, and a metal wire through which the first touch chip connects with the solid steel needle, and when the suction tube component is in a state of collecting liquid, the end face of the solid steel needle is located above a horizontal plane of the opening of the first conduit.

As a further improvement, the end face of the solid steel needle in the cavity does not exceed a vertical plane of the opening of the suction tube.

As a further improvement, the device for collecting liquid comprises a touch chip. A metal sleeve is sheathed outside the suction tube. The first conduit is a conductive hollow steel needle. The touch chip is connected to the first conduit through the metal wire. The touch chip, the metal wire, the first conduit and the metal sleeve form the liquid-level sensing mechanism, wherein the metal sleeve is provided with a liquid-suction inlet overlapped with the opening of the suction tube.

As a further improvement, the device for collecting liquid comprises a touch chip. A metal sleeve is sheathed outside the suction tube, the suction tube is internally provided with a second conduit for discharging the residual liquid in the cavity, the second conduit is a conductive hollow steel needle. The touch chip is connected to the second conduit through the metal wire. The touch chip, the metal wire, the second conduit and the metal sleeve form the liquid-level sensing mechanism, wherein the metal sleeve is provided with a liquid-suction inlet overlapped with the opening of the suction tube.

As a further improvement, the device for collecting liquid comprises a touch chip. A metal sleeve is sheathed outside the suction tube, the suction tube is internally provided with a second conduit for discharging the residual liquid in the cavity. Both the second conduit and the first conduit are conductive hollow steel needles. The touch chip is connected to the second conduit through the metal wire. The touch chip, the metal wire, the second conduit, the first conduit and the metal sleeve form the liquid-level sensing mechanism, wherein the metal sleeve is provided with a liquid-suction inlet that is overlapped with the opening of the suction tube.

As a further improvement, the bottom face of the metal sleeve is provided with a liquid-discharging outlet.

As a further improvement, a seal ring is disposed between the metal sleeve and the suction tube, the seal ring is disposed in the sides, which are proximate to the slide rail component, of both of the liquid-suction inlet and the liquid-discharging outlet.

As a further improvement, a sliding mechanism is further disposed between the fixing support and the swinging mechanism, the sliding mechanism comprises a mechanical transmission mechanism and a sliding support driven by the mechanical transmission mechanism to slide horizontally, and the swinging mechanism is disposed on the sliding support.

As a further improvement, the mechanical drive mechanism comprises a screw rod and a motor driving the screw rod to rotate, the screw rod is rotatably fixed in the fixing support, the sliding support is provided with an internal thread matched with an external thread of the screw rod, the sliding support slides parallelly along the screw rod with the driving of the motor.

As a further improvement, the sliding mechanism further comprises a round limiting bar in parallel with the screw rod and disposed in the fixing support, the sliding support is provided with a through-hole penetrating the round limiting bar.

As a further improvement, the device for collecting liquid further comprises a first optocoupler or a first Hall sensor for locating the position of the sliding support; a second optocoupler or a second Hall sensor for locating the position of the suction tube assembly, and a third optocoupler or a third Hall sensor for locating the position of the suction tube component.

As a further improvement, the swinging mechanism comprises a motor and a gear pair connected to the motor. The gear pair comprises a first gear connected to a main shaft of the motor and a second gear connected to the slide rail component. The first gear is meshed with the second gear. The motor drives the slide rail component to swing through the gear pair.

As a further improvement, the slide rail component is directly connected to the main shaft of the motor of the swinging mechanism.

As a further improvement, the suction tube assembly swings downwardly and outwardly under the effect of the swinging mechanism.

As a further improvement, when the suction tube assembly swings outwardly under the effect of the swinging mechanism, the suction tube assembly inclines downwardly with an angle of 5 to 30 degrees.

As a further improvement, the suction tube is internally provided with a second conduit for discharging the residual liquid in the cavity, and the second conduit is connected to a valve or a micro pump.

As a further improvement, the pump body mechanism comprises a plunger pump and a three-way electromagnetic valve. The three-way electromagnetic valve is connected to the first conduit, the plunger pump and a subsequent detection device respectively through the hose.

As a further improvement, the plunger pump further connects with an electromagnetic valve that is connected to a tap water pipe.

In addition, the present invention further provides a smart toilet, wherein the smart toilet comprises the device for collecting liquid described above, the fixing support is fixedly connected to the toilet body, the suction tube assembly swings towards the center of the toilet under the effect of the swinging mechanism, and the suction tube component is used for receiving the urine.

By employing the technical solutions above, the present invention has at least the following advantages.

The device in the present invention collects the urine in the air through the swingable and retractable suction tube assembly, which not only avoids contamination, but also can determine the end time through the real-time monitoring of the liquid-level sensing mechanism, thereby realizing a completely automatic collection process.

The present invention can flexibly achieve the accuracy, flexibility, convenience and reliability of sample positioning in the air through the cooperation among the sliding mechanism, the swinging mechanism and the retractable mechanism.

BRIEF DESCRIPTION OF THE FIGURES

The foregoing description is merely a summary of the technical solutions of the present invention. To understand the technical means of the present invention more clearly, the present invention is further described in details with reference to the figures and the specific embodiments hereinafter.

DETAILED DESCRIPTION OF THE INVENTION

In the embodiments, it is taken as an example that the device for collecting liquid is used as a device for collecting urine of a smart toilet to describe the device for collecting liquid in details, which should not be understood as any restriction on the device for collecting liquid.

First Embodiment

Figure 1:
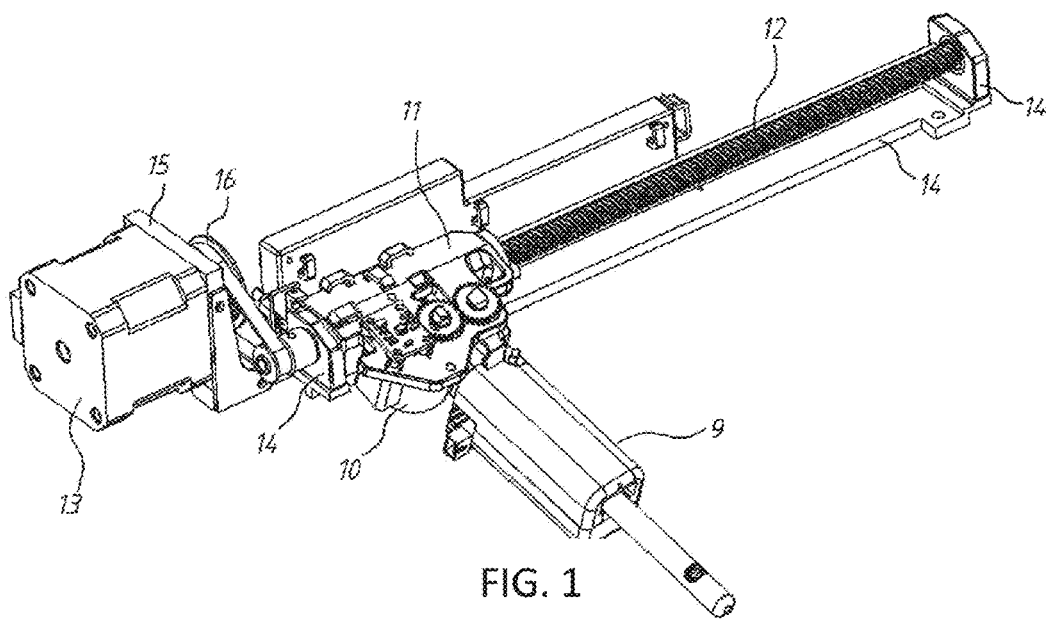
FIG. 1 is a schematic structure diagram of a suction tube assembly of a device for collecting liquid in an open state according to the present invention.
Figure 2:
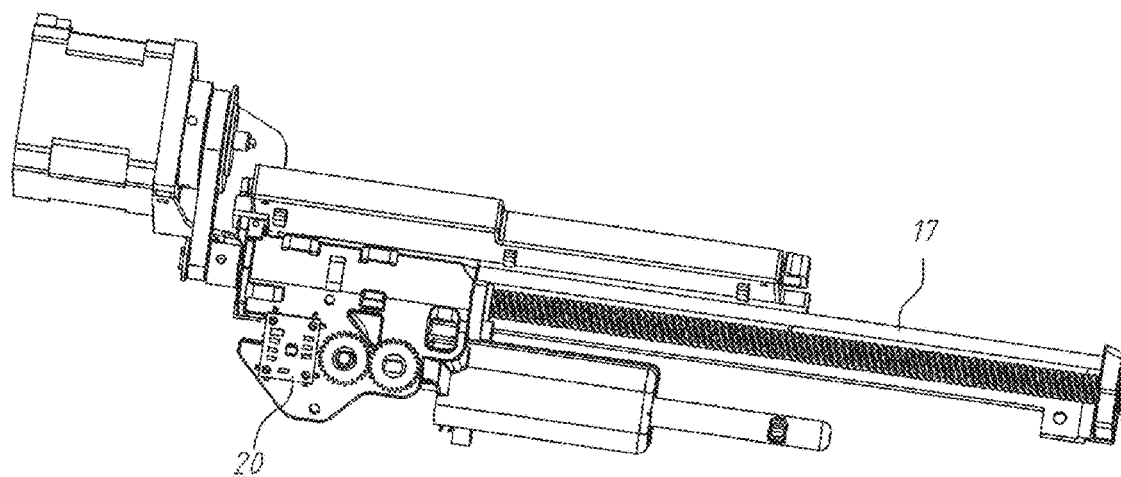
FIG. 2 is a schematic structure diagram of the suction tube assembly of the device for collecting liquid in a retraction state according to the present invention.
Figure 3:
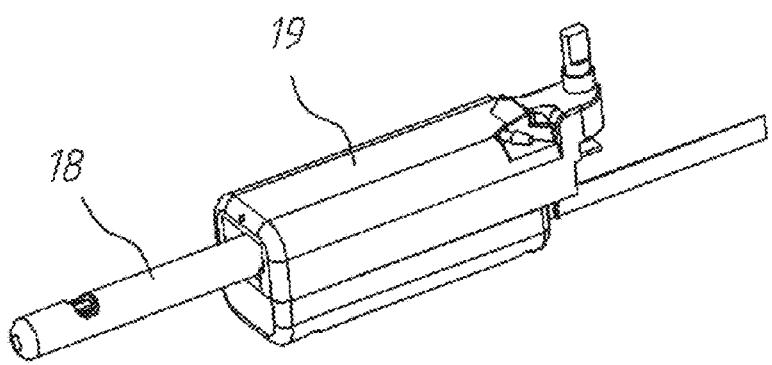
FIG. 3 is a schematic structure diagram of the suction tube assembly according to the present invention.

As shown in FIGS. 1 and 2, a device for collecting liquid in the present invention comprises a fixing support 14, a swinging mechanism 30 disposed in the fixing support 14, a suction tube assembly 9 connected to the swinging mechanism 30, and a pump body mechanism connected to the suction tube assembly 9.

The fixing support 14 is for being fixedly connected to a smart toilet. In this embodiment, the fixing support 14 is disposed in a long side edge of a toilet body, the suction tube assembly 9 swings towards the center of the toilet under the effect of the swinging mechanism 30 for receiving the urine in the air.

The swinging mechanism 30 comprises a gear motor 10, and a gear pair connected to the gear motor 10. The gear pair comprises a first gear connected to a main shaft of the gear motor and a second gear connected to the suction tube assembly, the first gear is meshed with the second gear, the gear motor 10 drives the suction tube assembly 9 to swing through the gear pair. Certainly, the suction tube assembly 9 can be directly connected to a main shaft of the motor of the swinging mechanism 30, and directly drives the suction tube assembly 9 to swing through the motor of the swinging mechanism 30. Any existing swinging mechanism 30 can further be adopted. Moreover, a preferred embodiment is that: the suction tube assembly 9 can swing downwardly and outwardly with certain degrees under the effect of the swinging mechanism 30, for example, downwardly incline with an angle less than 45 degrees, downwardly incline with an angle of 5 to 30 degrees is preferred, and downwardly incline with an angle of 20 degrees is optimal.

A sliding mechanism is further disposed between the fixing support 14 and the swinging mechanism 30, and a preferred embodiment of the sliding mechanism is that the sliding mechanism comprises a screw rod 12, a motor 13 driving the screw rod 12 to rotate, and a sliding support 11 disposed above the screw rod 12. The screw rod 12 is rotatably fixed on the fixing support 14. The motor 13 is preferably a first stepping motor, which is fixed on a motor hanging board 15 connected to the fixing support 14, and drives the screw rod 12 to rotate through mechanical transmission, the mechanical transmission is preferred to employ a synchronous belt and a synchronous pulley to realize the connection between the first stepping motor and the screw rod 12. The sliding support 11 is provided with an internal thread matched with an external thread of the screw rod 12. A screw rod pair transmission is formed between the sliding support 11 and the screw rod 12. Certainly, the sliding mechanism can further employ any existing horizontal sliding mechanical transmission mechanism.

As shown in FIG. 2, the sliding mechanism further comprises a round limiting bar 17 in parallel with the screw rod 12 and disposed on the fixing support 14. The sliding support 11 is provided with a through-hole penetrating the round limiting bar 17, which plays a role of limiting. The sliding support 11 slides along the screw rod 12 under the limiting effect of the round limiting bar 17. In order to reduce the friction force between the round limiting bar 17 and the sliding support 11, the round limiting bar is made of metal material. Certainly, the sliding support 11 can further slide along the screw rod 12 through a linear slide rail.

As shown in FIGS. 1 to 4, the suction tube assembly 9 is installed in the side of the sliding support 11, and comprises a slide rail component 19 and a retractable suction tube component 18 disposed in the slide rail component 19. The slide rail component 19 is internally provided with a second stepping motor and a slide rail, and the suction tube component 18 is retractable on the slide rail of the slide rail component 19 under the driving of the second stepping motor. Moreover, the suction tube component 18 is connected to the pump body mechanism.

Figure 5:
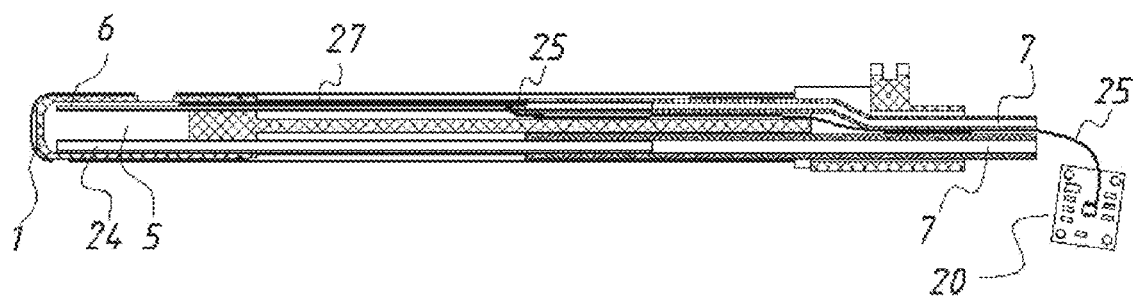
FIG. 5 is a cross-section schematic diagram of the first embodiment of the suction tube component according to the present invention.

As shown in FIG. 5, the suction tube component 18 comprises a suction tube 1, a first conduit 6 and a second conduit 24. The suction tube 1 is a pipeline, one end of which is internally provided with a cavity 5, and with an opening disposed above the cavity 5, the other end of which is provided with a sliding part cooperates with the slide rail above. The first conduit 6 is located above the second conduit 24, and is connected to the pump body mechanism through the hose 7. The other end of the second conduit 24 is connected to a valve or a micro pump through the hose for discharging the residual liquid or the washing sewage in the cavity 5. Preferably, the diameter of the second conduit 24 is greater than the one of the first conduit 6, which is advantageous for discharging the sewage. The pump body mechanism sucks the liquid in the cavity 5 through the hose 7 and the first conduit 6, so as for the detection of a subsequent device.

Figure 4:
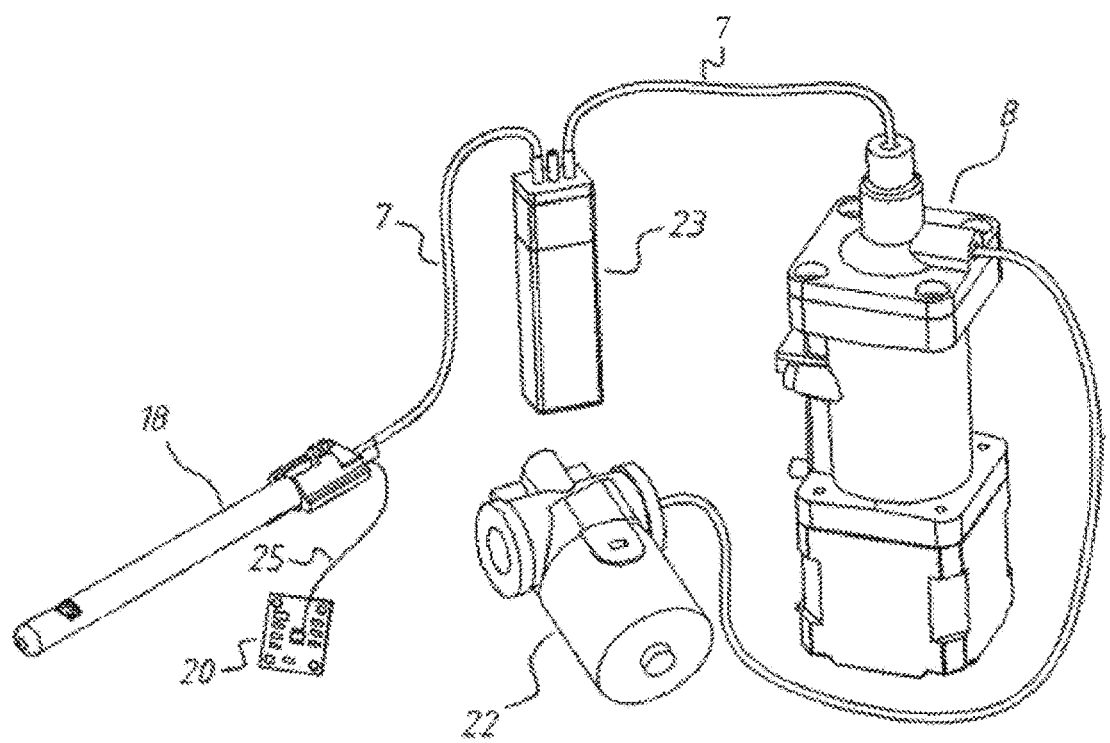
FIG. 4 is a schematic diagram illustrating a connection relationship between a suction tube component and a pump body mechanism according to the present invention.

The pump body mechanism described above further provides the function of cleaning. As shown in FIG. 4, the pump body mechanism in the embodiment comprises a plunger pump 8, and an electromagnetic valve 22 connected to the plunger pump 8, the plunger pump 8 is connected to a tap water pipe through the electromagnetic valve 22. When the suction tube component 18 needs to be cleaned, the electromagnetic valve 22 is opened, the plunger pump 8 pumps clean water into the cavity 5 through the hose 7 and the first conduit 6 for washing the cavity 5 and the pipeline intercommunicating with the cavity, and finally, the washing sewage flows out of the second conduit 24.

In order to realize the connection between the device for collecting liquid and the subsequent detection device, a three-way electromagnetic valve 23 is disposed between the suction tube component 18 and the plunger pump 8, the three ways of the three-way electromagnetic valve 23 are connected to the suction tube component 18, the plunger pump 8 and the subsequent detection device through the hose 7, respectively. The pump body mechanism can conveniently and flexibly switch among the three functions of absorbing the urine from the suction tube component 18, supplying the urine to the subsequent detection devices, and washing the suction tube component 18 and the subsequent detection devices.

When the device for collecting liquid of the present invention is in a non-working state, the sliding support 11 is located at one end of the screw rod 12, the position of which is called a mechanical zero of the suction tube, and the mechanical zero is determined by a first optocoupler disposed in the fixing support 14. The suction tube assembly 9 is disposed to be in parallel with the screw rod 12, the position of which is called a zero point of the polar coordinates of the suction tube, and the zero point of the polar coordinates is determined by a second optocoupler disposed in the sliding support 11. The suction tube component 18 is completely retracted into the slide rail component 19, such position is called a zero point of the axis coordinates of the suction tube, the zero point of the axis coordinates is determined by a third optocoupler disposed in the slide rail component 19. Certainly, the optocoupler locater can also finish the locating function through a Hall sensor.

When the device for collecting liquid of the present invention starts to work, the suction tube assembly 9 swings outwardly and downwardly with the driving of the gear motor 10 until being vertical to a long center shaft of the toilet, the suction tube component 18 extend out of the slide rail component 19 with the driving of a small-size stepping motor, and the sliding support 11 slides toward the middle of the screw rod 12 with the driving of the stepping motor 13, so that the suction tube assembly 9 reaches the center position of the toilet for collecting the urine.

Certainly, with the cooperation of a locating device that is capable of determining the direction of the fluid flow, the device for collecting liquid can also make the suction tube assembly 9 move along a direction of the screw rod 12 and at the same time the suction tube component 18 extends and retracts to reach a position right below the urine, then the urine enters the cavity 5 through a flat hole shaped liquid-suction inlet 3.

The present invention further comprises a liquid-level sensing mechanism for monitoring the amount of the urine in the cavity 5 in real time and controlling the start and stop of the pump body mechanism according to the amount of the urine in the cavity 5. When the amount of the urine reaches a threshold, the plunger pump 8 will automatically suck the urine in the cavity 5 for the subsequent device to detect; and at this time, the sliding support 11 returns to a mechanical zero of the suction tube, the suction tube assembly 9 swings back to the zero point of the polar coordinates of the suction tube, the suction tube component 18 returns to the zero point of the axis coordinates of the suction tube. When one urine detection is finished, the electromagnetic valve 22 connected to the plunger pump 8 is started to finish washing the device for collecting liquid.

Figure 6:
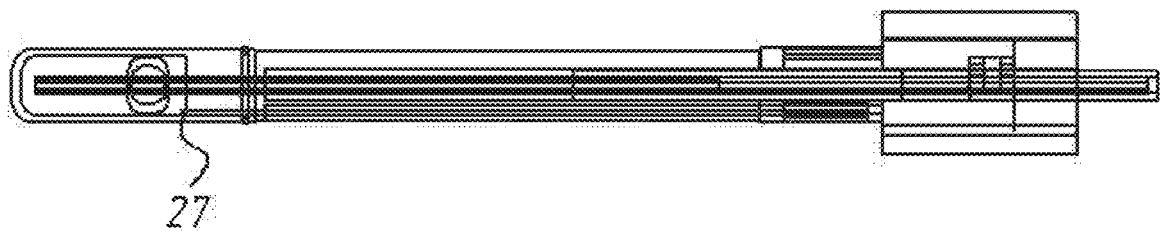
FIG. 6 is a structure schematic diagram of the first embodiment of the suction tube component according to the present invention.

As shown in FIGS. 5 and 6, the sliding support 11 is provided with a touch chip 20, the suction tube 1 is internally provided with a solid steel needle 27 with one end face inserted in the cavity 5, the touch chip 20 is connected to the solid steel needle 27 through the metal wire 25, and when the suction tube component 18 swings and is in a state of collecting liquid, the end face of the solid steel needle 27 in the cavity 5 should be located above a horizontal plane of the conduit opening of the first conduit 6; the touch chip 20, the metal wire 25 and the solid steel needle 27 form the liquid-level sensing mechanism, wherein the detection principle of the liquid-level sensing mechanism is that: when the amount of the urine sucked in the cavity 5 does not contact the end face of the solid steel needle 27, the input capacitance of the touch chip 20 is equal to the benchmark capacitance inside the chip plus the capacitance of the solid steel needle 27 outside the chip and the one of the metal wire 25. However, the capacitance of the solid steel needle 27 and the one of the metal wire 25 are very low, and can be neglected, at this time, the touch chip 20 outputs high level; when the cavity 5 is full of urine or the urine contacts the end face of the solid steel needle 27, the input capacitance from outside of the touch chip 20 is equal to the capacitance of the urine in the cavity 5 plus the one of the solid steel needle 27 and the one of the metal wire 25. Since compared with the capacitance of the solid steel needle 27 and the one of the metal wire 25, the capacitance of the urine in the cavity 5 is much higher, thus the input capacitance of the touch chip 20 is equal to the benchmark capacitance of the chip plus the capacitance of the urine in the cavity 5, at this time, the touch chip 20 outputs low level, at this time the pump body mechanism is started, the plunger pump 8 starts to suck the urine in the cavity 5. Moreover, the sliding support 11 returns to the mechanical zero point of the suction tube at the same time, the suction tube assembly 9 swings back to the zero point of the polar coordinates of the suction tube, the suction tube component 18 returns to the zero point of the axis coordinates of the suction tube. When one urine detection is finished, the electromagnetic valve 22 connected to the plunger pump 8 is started to finish washing the device for collecting liquid.

In order to satisfy the pump body to suck the amount of the urine in the cavity better, the end face of the solid steel needle 27 in the cavity does not exceed a vertical plane of the opening of the suction tube 1, which is advantageous for the cavity 5 to collect sufficient urine before starting to suck the urine when the suction tube component 18 incline downwardly.

Second Embodiment

Figure 7:
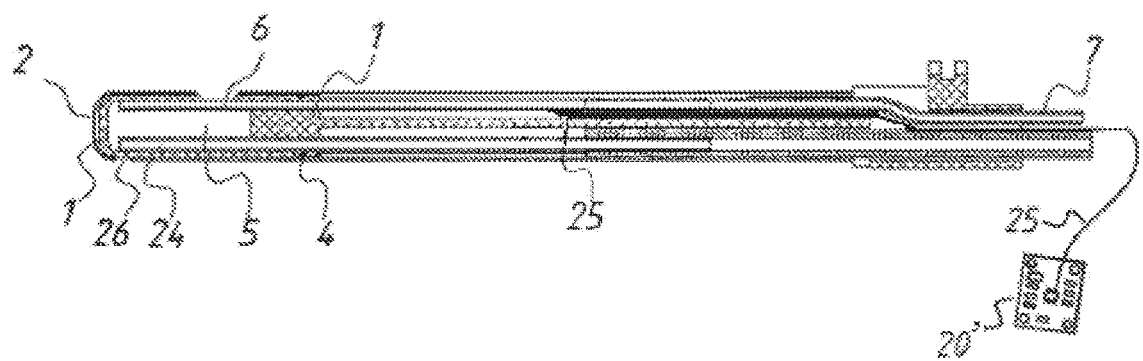
FIG. 7 is a cross-section schematic diagram of the second embodiment of the suction tube component according to the present invention.
Figure 8:
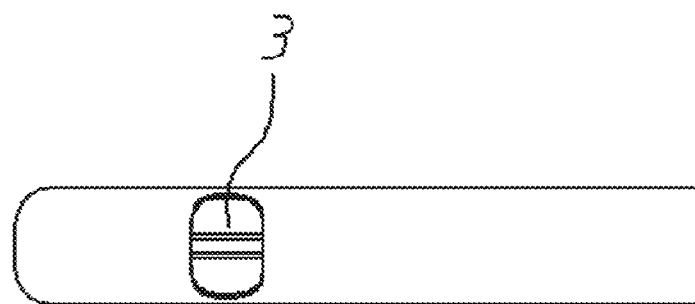
FIG. 8 is a structure schematic diagram of a liquid-suction inlet in the suction tube component according to the present invention.

Compared with the first embodiment, the second embodiment differs in the liquid-level sensing mechanism. The specific description is as follows:

As shown in FIGS. 7 and 8, the sliding support 11 is provided with a touch chip 20', a metal sleeve 2 is sheathed outside the suction tube 1, the metal sleeve 2 is provided with a liquid-suction inlet 3 overlapped with the opening of the suction tube 1. The first conduit 6 employs a conductive hollow steel needle. The touch chip 20' is connected to the first conduit 6 through metal wire 25. The metal sleeve 2, the first conduit 6, the metal wire 25 and the touch chip 20' form the liquid-level sensing mechanism, which monitors the amount of the urine stored in the cavity 5 in real time. The principle of the liquid-level sensing mechanism is as follows: when the cavity 5 has not sucked the urine, or the sucked amount of the urine does not reach the liquid-suction inlet 3, the first conduit 6 is disconnected from the metal sleeve 2; at this time, the input capacitance of the touch chip 20' is equal to the benchmark capacitance inside the chip plus the capacitance of the first conduit 6 outside the chip and the one of the metal wire 25, however the capacitance of the first conduit 6 and the one of the metal wire 25 are very low and can be neglected, thus the input capacitance of the touch chip 20' is still equal to the benchmark capacitance of the chip, the chip outputs high level; when the cavity 5 is full of urine, the first conduit 6 is in communication with the metal sleeve 2 via the urine at the liquid-suction inlet 3; at this time, the input capacitance from outside of the touch chip 20' is equal to the capacitance of the metal sleeve 2 plus the one of the first conduit 6 and the one of the metal wire 25. Since the capacitance of the metal sleeve 2 is very high, the input capacitance of the touch chip 20' is equal to the benchmark capacitance of the chip plus the capacitance of the metal sleeve 2, at this time the input capacitance of the touch chip 20' is higher than the threshold capacitance of the chip, and a low level is output. At this time, the pump body mechanism is started, and the plunger pump 8 starts to suck the urine in the cavity 5. Moreover, the sliding support 11 returns to the mechanical zero of the suction tube, the suction tube assembly 9 swings back to the zero point of the polar coordinates of the suction tube, the suction tube component 18 returns to the zero point of the axis coordinates of the suction tube. When one urine detection is finished, the electromagnetic valve 22 connected to the plunger pump 8 is started to finish washing the device for collecting liquid.

As a further improvement, a bottom face of the metal sleeve 2 is provided with a liquid-discharging outlet 26 for discharging the liquid entering a gap between the metal sleeve 2 and the suction tube 1 in time. Further, a seal ring 4 is disposed at the gap between the metal sleeve 2 and the suction tube 1, the seal ring 4 is disposed at the inner sides of the liquid-suction inlet 3 and of the liquid-discharging outlet 26 for preventing the liquid entering the gap between the metal sleeve 2 and the suction tube 1 from further flowing into the slide rail component 19.

Third Embodiment

Compared with the second embodiment described above, the third embodiment differs in that the second conduit 24 described above also uses a hollow steel needle made of metal material, the metal wire 25 described above connecting with the first conduit 6 is directly connected to the second conduit 24. The touch chip 20', the metal wire 25, the second conduit 24, the first conduit 6 and the metal sleeve 2 form the liquid-level sensing mechanism, and the detection principle of the liquid-level sensing mechanism is the same as that of the liquid-level sensing mechanism in the second embodiment above. All other structures are the same as the ones in the second embodiment, and will not be elaborated here.

Fourth Embodiment

Compared with the third embodiment, the fourth embodiment differs in that only the second conduit 24 uses a hollow steel needle made of metal material, while the first conduit 6 uses a non-conducting hollow conduit made of ordinary material. The touch chip 20', the metal wire 25, the second conduit 24 and the metal sleeve 2 form the liquid-level sensing mechanism, which is the same as the ones in the first embodiment and the second embodiment above, all for monitoring the amount of the urine collected in the cavity 5 in real time, and output low level or high level according to the amount of the liquid in the cavity 5, and the detection principles are similar. All other structures are the same as the ones in the third embodiment, and will not be elaborated here.

Four modes of the liquid-level sensing mechanisms as described above are used in the present invention to monitor the amount of the urine collected in the cavity in real time, so that the sample is automatically sucked and the suction tube assembly is automatically withdrawn after the amount of the urine in the cavity thereof satisfies the amount for detection. The automation of the device for collecting liquid is greatly improved, being convenient for use and being reliable for monitoring. Certainly, any existing liquid-level sensor can also be used to monitor the amount of the urine in the cavity in real time.

The device for collecting liquid of the present invention solves the problem of automatic urine suction of a smart toilet for health care. With such a device, the urine entering the toilet yet not reaching the internal surface of the toilet can be automatically collected, thus using the urine sucked in the air as a health analysis sample can avoid the cross-contamination problem caused by sucking the urine sample from the internal surface of the toilet. Certainly, the device for collecting liquid in the present invention can further be used in any field where collecting conductive sample in the air is required, so as to realize automatic sampling and improve the efficiency.

The foregoing description is merely preferred embodiments of the present invention, however, it is not intended to limit the present invention in any form, and any simple amendments, equivalent changes or modifications made by those skilled in the art using the technical contents disclosed above shall all fall within the protection scope of the present invention.

We claim:
1. A method for collecting liquid, the method comprising:
   collecting the liquid, by a pump body mechanism, into a cavity of a suction tube assembly;
   monitoring, by a liquid-level sensing mechanism, an amount of the liquid collected in the cavity;
   controlling, by the liquid-level sensing mechanism, a start and a stop of collecting the liquid in response to the amount of the liquid collected in the cavity; and
   cleaning the cavity by delivering, by the pump body mechanism, water into the cavity in response to the stop of collecting the liquid.
2. The method according to claim 1, further comprising:
   swing outwardly and downwardly, by a swing mechanism, the suction tube assembly to a predetermined position in a toilet; and
   extending, by a motor, a suction tube component from a slide rail component of the suction tube assembly.
3. The method according to claim 1,
   wherein the cleaning the cavity comprising:
      delivering, by a first conduit, the water into the cavity; and
      discharging, by a second conduit, a residual liquid in the cavity.
4. The method according to claim 3, further comprising:
   delivering, by the pump body mechanism and the first conduit, the liquid collected in the cavity to a subsequent device for a subsequent detection before cleaning the cavity.
5. The method according to claim 4, further comprising:
   switching, by a three-way electromagnetic valve, among collecting the liquid into the cavity, delivering the liquid collected in the cavity to the subsequent device for the subsequent detection, and cleaning the cavity.
6. The method according to claim 1, further comprising:
   determining, by the liquid-level sensing mechanism, whether the amount of the liquid collected in the cavity reaches a threshold,
   wherein the amount of the liquid collected in the cavity reaches the threshold based on a change in an input capacitance of the liquid-level sensing mechanism.
7. The method according to claim 6,
   wherein the liquid-level sensing mechanism comprises a touch chip, and
   wherein the determining whether the amount of the liquid collected in the cavity reaches the threshold based on the change in the input capacitance of the liquid-level sensing mechanism comprises:
      determining whether an input capacitance of the touch chip is increased.
8. The method according to claim 7, further comprising:
   forming the liquid-level sensing mechanism, comprising:
      inserting at least one portion of a needle into the cavity; and
      connecting the touch chip to the needle via a metal wire,
   wherein the determining whether the input capacitance of the touch chip is increased comprises:
      detecting a capacitance of the liquid collected in the cavity generated when the liquid collected in the cavity contacts the at least one portion of the needle.
9. The method according to claim 8, further comprising:
   determining the input capacitance of the touch chip as a sum of a benchmark capacitance inside the touch chip, a capacitance of the needle, and a capacitance of the metal wire when the liquid collected in the cavity does not contact the at least one portion of the needle; and
   determining the input capacitance of the touch chip as a sum of the capacitance of the liquid collected in the cavity, the benchmark capacitance inside the touch chip, the capacitance of the needle, and the capacitance of the metal wire when the liquid collected in the cavity contacts the at least one portion of the needle.
10. The method according to claim 9,
    wherein the forming the liquid-level sensing mechanism further comprises:
       inserting at least one portion of a first conduit into the cavity; and
       disposing the at least one portion of the needle above the at least one portion of the first conduit, and
    wherein the needle is a conductive solid needle comprising an end inserted in the cavity.
11. The method according to claim 7, further comprising:
    forming the liquid-level sensing mechanism by:
       sheathing a metal sleeve outside a suction tube of the suction tube assembly;
       inserting at least one portion of a first conduit into the cavity; and
       connecting the touch chip to the first conduit via a metal wire,
    wherein the determining whether the input capacitance of the touch chip is increased comprises:
       detecting a capacitance of the metal sleeve generated when the metal sleeve is in communication with the at least one portion of the first conduit via the liquid collected in the cavity.

12. The method according to claim 11, further comprising:
    determining the input capacitance of the touch chip as a sum of a benchmark capacitance inside the touch chip, a capacitance of the first conduit, and a capacitance of the metal wire when the metal sleeve is not in communication with the at least one portion of the first conduit; and
    determining the input capacitance of the touch chip as a sum of the capacitance of the metal sleeve, the benchmark capacitance inside the touch chip, the capacitance of the first conduit, and the capacitance of the metal wire when the metal sleeve is in communication with the at least one portion of the first conduit via the liquid collected in the cavity.

13. The method according to claim 12,
wherein the first conduit is a conductive hollow needle.

14. The method according to claim 7, further comprising:
forming the liquid-level sensing mechanism by:
    sheathing a metal sleeve outside a suction tube of the suction tube assembly;
    inserting at least one portion of a first conduit and at least one portion of a second conduit into the cavity; and
    connecting the touch chip to the second conduit via a metal wire,
wherein the determining whether the input capacitance of the touch chip is increased comprises:
    detecting a capacitance of the metal sleeve generated when the metal sleeve is in communication with the at least one portion of the first conduit via the liquid collected in the cavity.

15. The method according to claim 14,
wherein the first conduit and the second conduit are both conductive hollow needles.

16. The method according to claim 14,
wherein the first conduit is a non-conductive hollow needle, and the second conduit is a conductive hollow needle.

17. A system for collecting liquid, the system comprising:
a controller;
a pump body mechanism communicably coupled to the controller and configured, in response to a command of the controller, to:
    collect the liquid into a cavity of a suction tube assembly; and
    delivering water into the cavity to clean the cavity; and
a liquid-level sensing mechanism communicably coupled to the controller and comprising a touch chip, the liquid-level sensing mechanism configured, in response to a command of the controller, to:
    determine whether an amount of the liquid collected in the cavity reaches a threshold based on a change in an input capacitance of the touch chip; and
    control a start and a stop of collecting the liquid in response to the amount of the liquid collected in the cavity.

18. The system according to claim 17,
wherein the liquid-level sensing mechanism is formed by the touch chip and a needle inserted into the cavity and connected to the touch chip via a metal wire, and
wherein the liquid-level sensing mechanism determines that the amount of the liquid collected in the cavity reaches the threshold in response to a detection of a capacitance of the liquid collected in the cavity generated when the liquid collected in the cavity contacts the needle.

19. The system according to claim 17,
wherein the liquid-level sensing mechanism is formed by the touch chip, a first conduit inserted into the cavity and connected to the touch chip via a metal wire, and a metal sleeve sheathed outside a suction tube of the suction tube assembly, and
wherein the liquid-level sensing mechanism determines that the amount of the liquid collected in the cavity reaches the threshold in response to a detection of a capacitance of the metal sleeve generated when the metal sleeve is in communication with the first conduit via the liquid collected in the cavity.

20. The system according to claim 17,
wherein the liquid-level sensing mechanism is formed by the touch chip, a first conduit inserted into the cavity, a second conduit inserted into the cavity and connected to the touch chip via a metal wire, and a metal sleeve sheathed outside a suction tube of the suction tube assembly, and
wherein the liquid-level sensing mechanism determines that the amount of the liquid collected in the cavity reaches the threshold in response to a detection of a capacitance of the metal sleeve generated when the metal sleeve is in communication with the first conduit via the liquid collected in the cavity.

* * * * *